United States Patent
Ranucci et al.

(10) Patent No.: US 9,339,271 B2
(45) Date of Patent: May 17, 2016

(54) ARTICULATING SURGICAL INSTRUMENTS

(71) Applicant: C.R. Bard, Inc., Murray Hill, NJ (US)

(72) Inventors: Kevin J. Ranucci, Warwick, RI (US); Nathan Stewart Cauldwell, Mansfield, MA (US); Augustus Felix, Cranston, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 569 days.

(21) Appl. No.: 13/827,254

(22) Filed: Mar. 14, 2013

(65) Prior Publication Data

US 2014/0276966 A1 Sep. 18, 2014

(51) Int. Cl.
| | |
|---|---|
| *A61B 17/072* | (2006.01) |
| *A61B 17/10* | (2006.01) |
| *A61B 17/00* | (2006.01) |
| *A61M 25/01* | (2006.01) |
| *A61B 17/068* | (2006.01) |
| *A61M 25/06* | (2006.01) |
| *A61B 17/29* | (2006.01) |
| *A61B 17/064* | (2006.01) |

(52) U.S. Cl.
CPC ............ *A61B 17/10* (2013.01); *A61B 17/00234* (2013.01); *A61B 17/068* (2013.01); *A61B 17/07207* (2013.01); *A61B 17/29* (2013.01); *A61M 25/0138* (2013.01); *A61M 25/0147* (2013.01); *A61B 2017/003* (2013.01); *A61B 2017/00309* (2013.01); *A61B 2017/0647* (2013.01); *A61B 2017/2905* (2013.01); *A61B 2017/2908* (2013.01); *A61B 2017/2927* (2013.01); *A61M 25/0662* (2013.01)

(58) Field of Classification Search
CPC ............ A61B 17/00491; A61B 17/29; A61B 17/068; A61B 17/0686; A61B 17/072; A61B 17/07207; A61B 17/0087; A61B 17/00234; A61B 1/018; A61B 1/0016; A61B 1/0052; A61B 1/00133; A61B 1/00135; A61B 2017/003; A61B 2017/00309; A61B 2017/00314; A61B 2017/2905; A61B 2017/2919; A61B 2017/2927; A61B 2017/00292; A61B 2017/07271; A61M 25/00; A61M 25/0068; A61M 25/0662; A61M 25/0074; A61M 25/0138; A61M 25/0152; A61M 25/0147
USPC ............... 227/19, 175.1, 175.2, 176.1, 180.1; 606/49, 51, 45, 139, 143, 205, 207, 606/208, 219
See application file for complete search history.

(56) References Cited

U.S. PATENT DOCUMENTS

| | | |
|---|---|---|
| 3,802,440 A | 4/1974 | Salem et al. |
| 5,325,845 A | 7/1994 | Adair |

(Continued)

FOREIGN PATENT DOCUMENTS

WO WO 2006/119495 A2 11/2006

*Primary Examiner* — Scott A. Smith
(74) *Attorney, Agent, or Firm* — Wolf, Greenfield & Sacks, P.C.

(57) ABSTRACT

A surgical instrument and its method of use are disclosed. In one embodiment, the surgical instrument may include a handle and an elongated shaft assembly extending distally from the handle. The elongated shaft assembly may include an articulable portion with an articulation direction. The elongated shaft assembly may also include a tubular member with a flexible portion with a preferential bending direction and a direction of bending resistance. The tubular member may permit articulation of the elongated shaft assembly when the preferential bending direction is aligned with the articulation direction.

28 Claims, 8 Drawing Sheets

(56) References Cited

U.S. PATENT DOCUMENTS

| | | | |
|---|---|---|---|
| 5,381,782 A | 1/1995 | DeLaRama et al. | |
| 5,417,203 A | 5/1995 | Tovey et al. | |
| 5,501,654 A | 3/1996 | Failla et al. | |
| 5,609,601 A | 3/1997 | Kolesa et al. | |
| 5,643,294 A | 7/1997 | Tovey et al. | |
| 5,669,926 A | 9/1997 | Aust et al. | |
| 5,704,534 A * | 1/1998 | Huitema | A61B 17/07207 227/175.1 |
| 5,715,817 A * | 2/1998 | Stevens-Wright | A61B 18/1492 600/373 |
| 5,766,196 A | 6/1998 | Griffiths | |
| 5,823,066 A * | 10/1998 | Huitema | A61B 17/07207 227/175.1 |
| 5,836,960 A | 11/1998 | Kolesa et al. | |
| 5,851,212 A | 12/1998 | Zirps et al. | |
| 5,921,956 A | 7/1999 | Grinberg et al. | |
| 6,048,339 A | 4/2000 | Zirps et al. | |
| 6,146,338 A | 11/2000 | Gardeski et al. | |
| 6,171,316 B1 * | 1/2001 | Kovac | A61B 17/062 606/144 |
| 6,485,440 B1 | 11/2002 | Gardeski | |
| 6,656,195 B2 | 12/2003 | Peters et al. | |
| 6,749,560 B1 * | 6/2004 | Konstorum | A61B 1/00071 600/139 |
| 7,008,375 B2 | 3/2006 | Weisel | |
| 7,101,371 B2 * | 9/2006 | Dycus | A61B 18/1445 606/205 |
| 7,413,543 B2 | 8/2008 | Banik et al. | |
| 7,678,117 B2 * | 3/2010 | Hinman | A61B 1/0055 606/1 |
| 7,682,319 B2 * | 3/2010 | Martin | A61B 17/00234 600/139 |
| 7,771,416 B2 * | 8/2010 | Spivey | A61B 1/00133 600/106 |
| 7,785,252 B2 * | 8/2010 | Danitz | A61B 1/0071 138/118 |
| 7,842,028 B2 * | 11/2010 | Lee | A61B 17/062 600/114 |
| 7,909,220 B2 * | 3/2011 | Viola | A61B 17/07207 227/175.1 |
| 7,918,376 B1 | 4/2011 | Knodel et al. | |
| 7,955,315 B2 * | 6/2011 | Feinberg | A61B 17/00491 604/528 |
| 8,052,597 B2 * | 11/2011 | Boulais | A61B 1/00103 600/141 |
| 8,097,003 B2 * | 1/2012 | Hoffman | A61B 17/12013 606/139 |
| 8,157,834 B2 * | 4/2012 | Conlon | A61B 17/29 606/205 |
| 8,236,010 B2 * | 8/2012 | Ortiz | A61B 17/068 227/175.1 |
| 8,262,563 B2 * | 9/2012 | Bakos | A61B 1/00135 600/114 |
| 2006/0241564 A1 | 10/2006 | Corcoran et al. | |
| 2007/0282358 A1 | 12/2007 | Remiszewski et al. | |
| 2009/0090764 A1 | 4/2009 | Viola | |
| 2010/0010299 A1 | 1/2010 | Bakos et al. | |
| 2010/0191050 A1 | 7/2010 | Zwolinski | |
| 2010/0331776 A1 | 12/2010 | Salahieh et al. | |
| 2011/0230718 A1 | 9/2011 | Akui | |
| 2012/0123395 A1 | 5/2012 | Stoy et al. | |
| 2012/0130173 A1 | 5/2012 | Lutze et al. | |
| 2012/0143175 A1 | 6/2012 | Hermann et al. | |
| 2013/0023923 A1 | 1/2013 | Mueller | |

* cited by examiner

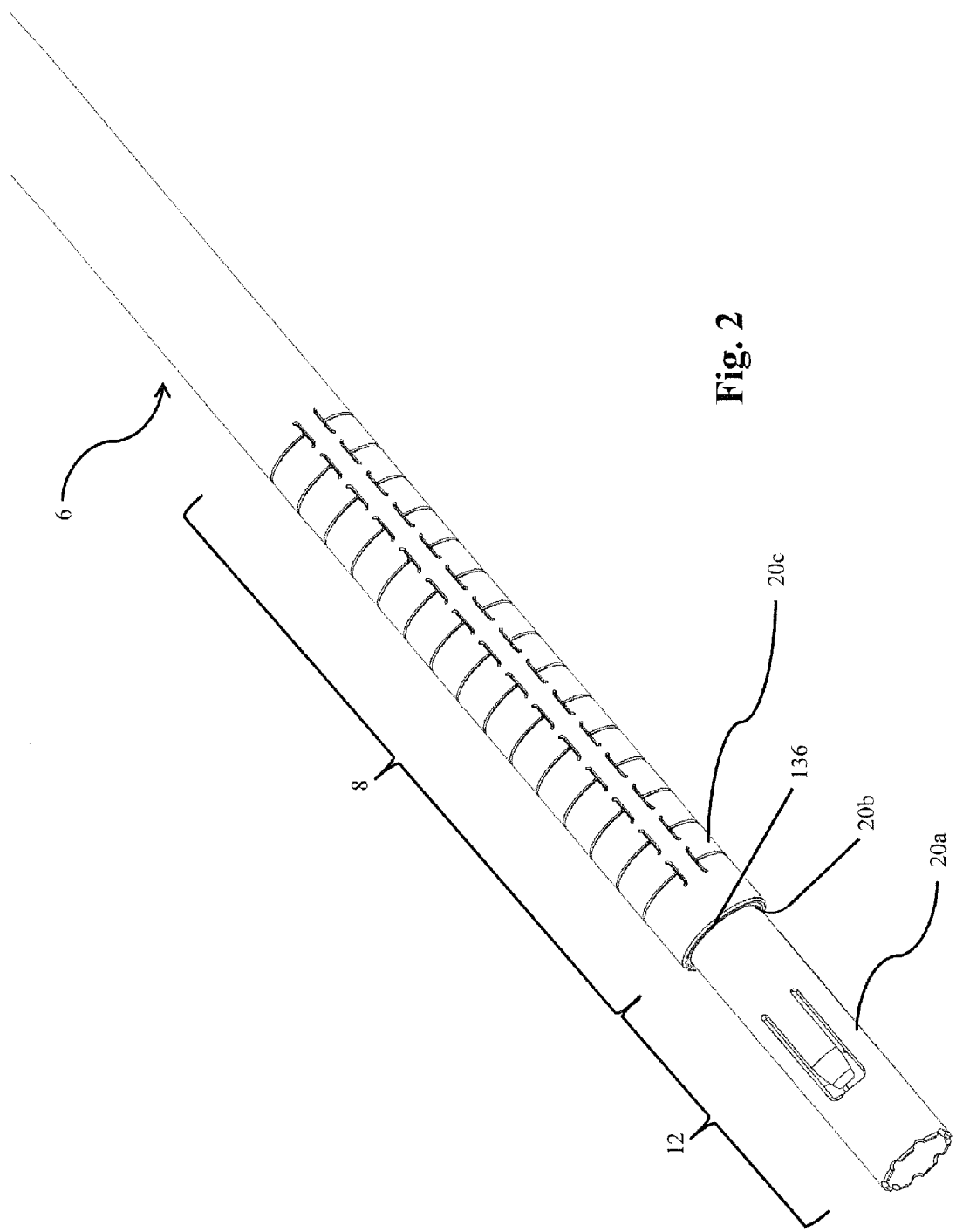

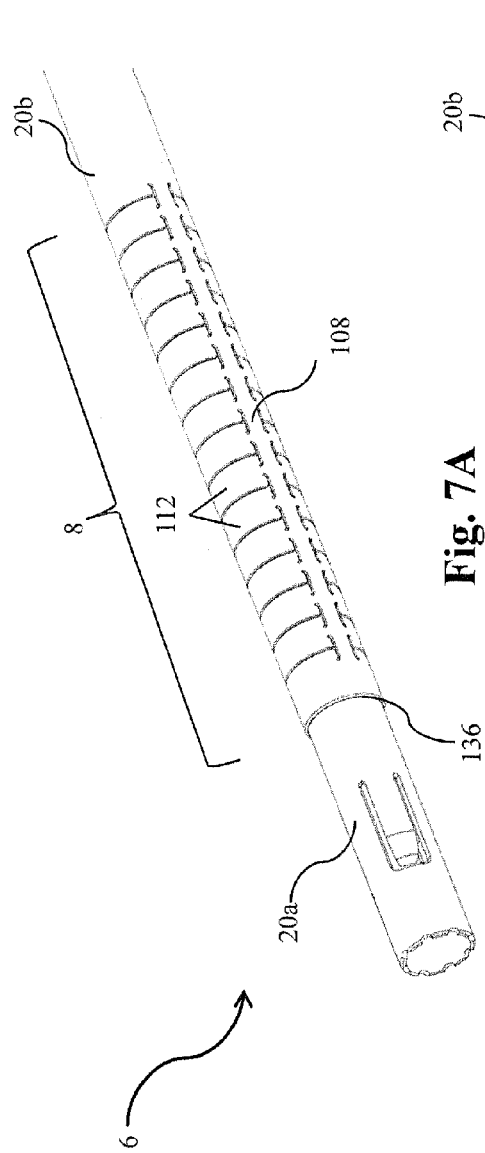
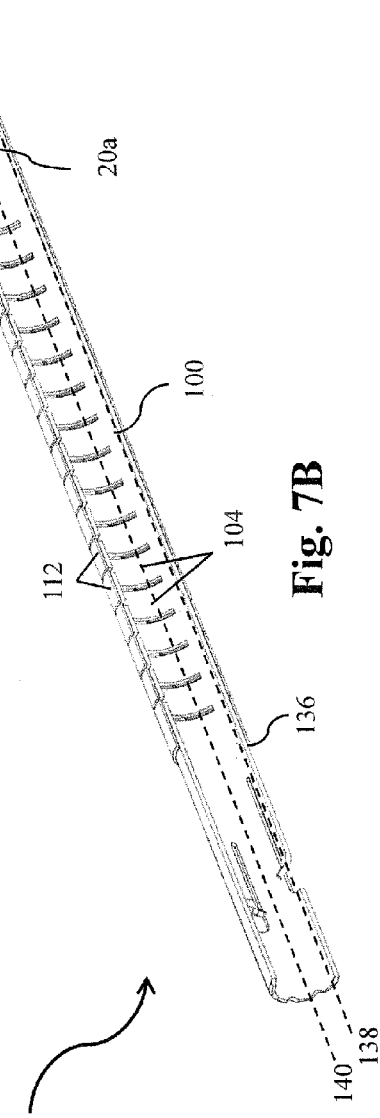
Fig. 7A
Fig. 7B

ARTICULATING SURGICAL INSTRUMENTS

FIELD

Articulating surgical instruments.

BACKGROUND

A surgical mesh fabric or other prosthetic repair fabric may be used to surgically repair a hernia. The prosthetic repair fabric is typically placed in an open procedure or laparoscopically. Oftentimes a surgical instrument is used to secure the repair fabric in place by deploying one or more fasteners from a distal end of the surgical instrument through the prosthetic repair fabric and into the underlying tissue. However, a surgical instrument that includes a rigid elongated shaft assembly for deploying the fasteners may have a limited range of motion within the surgical field. Consequently, many surgical instruments include at least one articulable portion along the elongated shaft assembly to facilitate the orientation and placement of fasteners within the surgical field.

SUMMARY

In one embodiment, a surgical instrument includes a handle and an elongated shaft assembly extending distally from the handle. The elongated shaft assembly includes an articulable portion with an articulation direction. The elongated shaft assembly also includes a tubular member with a flexible portion with a preferential bending direction and a direction of bending resistance. The tubular member permits articulation of the elongated shaft assembly when the preferential bending direction is aligned with the articulation direction.

In another embodiment, a surgical instrument includes a handle and an elongated shaft assembly extending distally from the handle. The elongated shaft assembly includes a first tubular member including a first flexible portion with a first preferential bending direction, a second tubular member including a second flexible portion with a second preferential bending direction, and a third tubular member including a third flexible portion with a third preferential bending direction and a direction of bending resistance. The first tubular member, the second tubular member, and the third tubular member are coaxially located. The first tubular member and the second tubular member are axially fixed relative to one another at a position distal from the first flexible portion and the second flexible portion. The third tubular member is displaceable relative to the first tubular member and the second tubular member.

In yet another embodiment, a surgical instrument includes a handle and an elongated shaft assembly extending distally from the handle. The elongated shaft assembly includes a first tubular member including a first flexible portion with a first spine, a second tubular member including a second flexible portion with a second spine, and a third tubular member including a third flexible portion with a third spine and a fourth spine. The first tubular member, the second tubular member, and the third tubular member are coaxially located. The first tubular member and the second tubular member are also axially fixed relative to one another at a position distal from the first flexible portion and the second flexible portion. Additionally, the third tubular member is displaceable relative to the first tubular member and the second tubular member.

In another embodiment, a surgical instrument includes a handle and an elongated shaft assembly extending distally from the handle. The elongated shaft assembly includes a first tubular member including a first flexible portion with a first spine and a second tubular member including a second flexible portion with a second spine and a third spine. The first tubular member and the second tubular member are coaxially located. Additionally, the first tubular member and the second tubular member are axially fixed relative to one another at a position distal from the first flexible portion and the second flexible portion. The second tubular member is also rotatable relative to the first tubular member.

In yet another embodiment, a method of operating a surgical instrument includes: providing: a handle; an elongated shaft assembly extending distally from the handle, wherein the elongated shaft assembly includes an articulable portion with an articulation direction, and wherein the elongated shaft assembly includes a tubular member with a flexible portion with a preferential bending direction and a direction of bending resistance; and displacing the tubular member to selectively align the preferential bending direction of the tubular member with the articulation direction of the elongated shaft assembly to permit articulation of the elongated shaft assembly.

It should be appreciated that the foregoing concepts, and additional concepts discussed below, may be arranged in any suitable combination, as the present disclosure is not limited in this respect. Further, the foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 2 is a schematic representation of an articulable portion of an elongated shaft assembly;

FIG. 7A is a schematic perspective view of the distal portion of the inner and intermediate tubular members;

FIG. 7B is a cross-sectional view of the inner and intermediate tubular members depicted in FIG. 7A;

DETAILED DESCRIPTION

Figure 1:
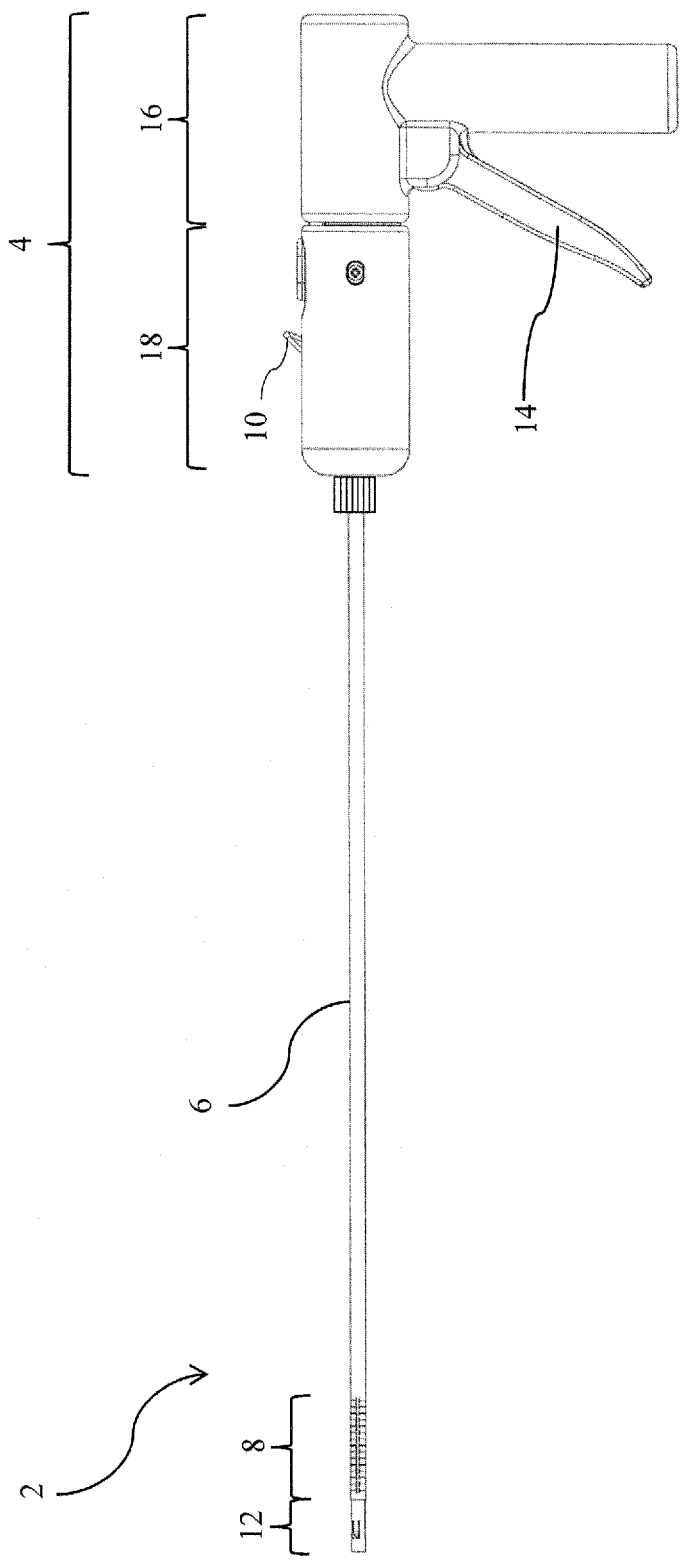
FIG. 1 is a schematic representation of an articulable surgical instrument.

The inventors have recognized that it may be desirable to selectively permit or prevent the articulation of a surgical instrument in particular instances. For example, it may be desirable to prevent the articulation of a surgical instrument during the insertion and extraction of the surgical instrument into a surgical field as might occur during laparoscopic surgery.

In one embodiment, an elongated shaft assembly extends distally from the handle of a surgical instrument and includes an articulable portion. The articulable portion of the elongated shaft assembly may articulate in at least one direction between a first position, such as an unarticulated position, and a second position, such as a fully articulated position. In addition to the elongated shaft assembly, the surgical instrument may include a rotatable tubular member with a flexible portion that is associated with the articulable portion of the elongated shaft assembly. For example, the flexible portion of the tubular member may be axially aligned and at least partially coextensive with the articulable portion of the elongated shaft assembly. The flexible portion of the tubular member may have a preferential bending direction as well as a direction of bending resistance. Rotation of the tubular member relative to the articulable portion of the elongated shaft assembly may selectively align either the preferential bending direction or the direction of bending resistance of the flexible portion with the articulation direction of the elongated shaft assembly. When the preferential bending direction of the flexible portion is aligned with the articulation direction, the elongated shaft assembly may articulate. In contrast, when the direction of bending resistance of the flexible portion is aligned with the articulation direction, articulation of the elongated shaft assembly may be prevented. Thus, rotation of the tubular member relative to the articulable portion of the elongated shaft assembly may selectively permit or prevent articulation of the surgical instrument.

The various tubular members associated with the articulation locking mechanism as well as the articulable portion of the elongated shaft assembly may be constructed and arranged in any number of ways to provide one or more preferential bending directions and/or directions of bending resistance. For example, in one embodiment, a tubular member may include one or more weakened sections along one or more sides of the tubular member to provide one or more preferential bending directions and directions of bending resistance. These weakened sections may be provided by: an appropriate pattern of slots, cuts, and/or spines; composite structures of flexible and rigid materials; combinations of the above; or any other appropriate construction. Alternatively, in some embodiments, a tubular member might include a plurality of interconnected segments to form the flexible portion. These interconnected segments could be constructed and arranged to permit movement in one or more directions, corresponding to preferential bending directions and resist movement in one or more directions corresponding to directions of bending resistance. For example, the interconnected segments may only have a single axis of rotation due to the use of pin joints in the same orientations to connect the segments thus permitting pivoting of adjacent interconnected segments in one direction and resisting all other directions of movement.

While several possible embodiments related to the construction of the articulable elongated shaft assembly are described herein, it should be understood that the current disclosure is not limited to only the described embodiments. For example, the articulable portion of the elongated shaft assembly may be constructed and arranged in any appropriate fashion to provide articulation in a desired direction. Further, while a specific type of articulation mechanism using tubular members with offset neutral bending axes is described, the currently disclosed articulation locking mechanism may be used with any appropriate method of articulating an elongated shaft assembly. For example the articulable portion of the elongated shaft assembly may be articulated using: one or more control wires, ribbons, or slats associated with the articulable portion; prestressed members and retractable sheaths, rigid linkages associated with pivot joints; or any other appropriate structure capable of articulating the articulable portion.

In addition to the above, while several patterns of slots and spines are disclosed regarding the flexible portions of the tubular members, it should be understood that other patterns of slots and spines are also possible. For example, the flexible portions of the tubular members corresponding to the articulable portion of the elongated shaft assembly may be constructed and arranged in any appropriate fashion such that the flexible portion preferentially bends in at least one direction and provides an increased resistance to bending in at least one other direction.

For the sake of clarity, the currently disclosed embodiments discussed below in regards to the figures are directed to a laparoscopic device for deploying one or more fasteners. However, the current disclosure is not limited to laparoscopic devices for deploying one or more fasteners. Instead, the disclosed articulation locking mechanisms could be used in any appropriate surgical instrument including an articulable portion. For example, an articulation locking mechanism, as disclosed herein, could be incorporated into an endoscopic device, a borescopic device, a catheter, a surgical instrument for use in "open" procedures, or any other appropriate surgical instrument. Further, the disclosed surgical instruments may include any appropriate end effector and are not limited to the deployment of fasteners. However, in those embodiments including fasteners, the instrument including the articulation locking mechanism may be loaded with one or more fasteners, or it may be constructed to allow the user to load the instrument with one or more fasteners. In addition, disclosed embodiments that include fasteners are described with regards to a generic fastener. Consequently, it should also be understood that any appropriate fastener might be used with the currently disclosed articulation locking mechanisms including a tack, a clip, a staple, a pin, a tissue anchor, a bone anchor, or any other appropriate type of fastener.

Turning now to the figures, specific embodiments of an articulation locking mechanism incorporated into a surgical instrument are described.

FIG. 1 presents one embodiment of a surgical instrument 2. The surgical instrument includes a handle 4 and an elongated shaft assembly 6 extending distally from the handle 4. In addition to fasteners being deployed from a distal end of the elongated shaft assembly 6, the elongated shaft assembly may include an articulable portion 8. Articulation of the articulable portion 8 may be controlled by an articulation control 10 which may be moved between one or more positions to shift articulable portion 8 to a desired articulation angle. The surgical instrument 2 may also include a trigger 12 for actuating a fastener deployment system 210 to deploy a fastener, see FIG. 12.

The articulable portion 8 depicted in FIG. 1 may be shifted between a first position, such as an unarticulated (i.e. straight) position, and second position, such as a fully articulated position, using the articulation control 10. Depending on the embodiment, the articulable portion 8 may be shifted to one or more preselected articulation angles, or the articulable portion 8 may be adjusted to one or more arbitrary (i.e. not preselected) articulation angles. The articulable portion 8 may be articulated in at least a first direction. Embodiments in which the articulable portion articulates in at least a second direction are also envisioned. For example, the articulable portion 8 may be articulated in a first direction corresponding to an articulation angle greater than approximately 0° and in a second direction corresponding to an articulation angle less than approximately 0°. Alternatively, or in addition to the above, the articulable portion 8 might be articulated about two different axes (e.g. articulation in the horizontal direction and the vertical direction) such that it articulates in at least two directions.

Figure 12:
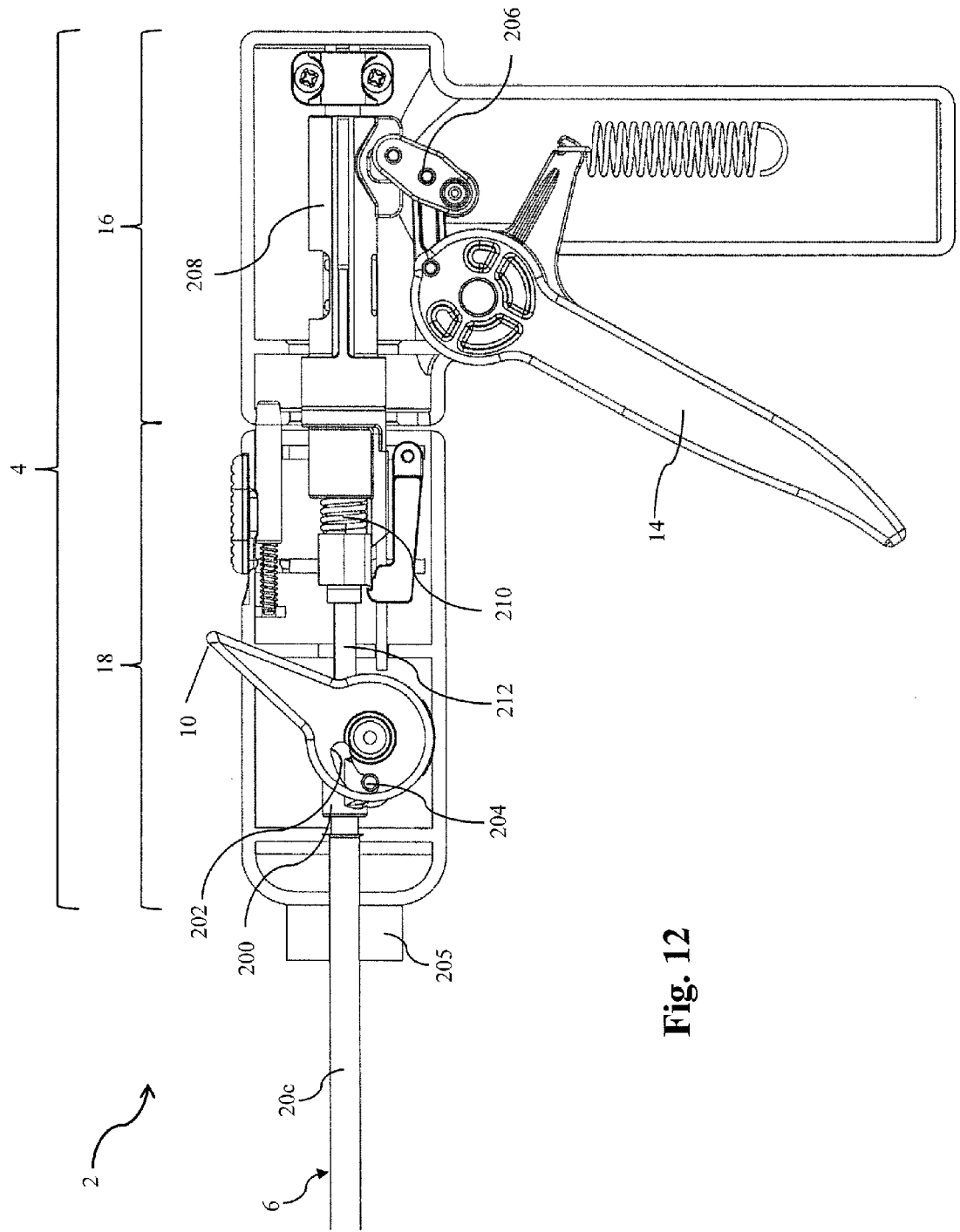
FIG. 12 is a schematic representation of the interior of the surgical instrument handle.

In some embodiments, it may be desirable to rotate the elongated shaft assembly 6 to facilitate positioning of the distal tip. One such embodiment is depicted in FIGS. 1 and 12. The rotation of the elongated shaft assembly 6 may be provided in any appropriate manner. For example, the elongated shaft assembly 6 may simply be adapted to be rotatable to at least a portion of the handle 4. Alternatively, a portion of the handle 4 including the elongated shaft assembly 6 may be rotatable relative to a another portion of the handle 4, such as the portion including the grip. One such embodiment is depicted in FIG. 1. In the depicted embodiment, the surgical instrument 2 includes a first handle portion 16 and a second handle portion 18 including the elongated shaft assembly 6. The first and second handle portions 16 and 18 may be constructed and arranged in any appropriate fashion to be rotatable relative to one another. It should be understood that while a surgical instrument including a rotatable elongated shaft assembly 6 or handle 4 is depicted in the figures, a surgical instrument including a unitary handle and/or an elongated shaft assembly 6 that is stationary relative to the handle are also possible as the current disclosure is not limited in this manner.

In certain applications, it may be advantageous to include a distal rigid straight portion 12 that is distally located from the articulable portion 8. The rigid straight portion 12 may include a number of features to aid in the deployment of fasteners from the distal end of the elongated shaft assembly 6. For example, the distal rigid straight portion 12 may include fastener retaining elements such as tabs to retain a distal most fastener in a fastener deployment position prior to actuation of the surgical instrument. Additionally, without wishing to be bound by theory, when a driveshaft of a fastener deployment system applies a force to a fastener as it goes around an articulated portion of the elongated shaft assembly, the force applied by the drive shaft to the head of the fastener may not be fully aligned with the deployment direction of the associated fastener. Thus, it may be desirable to include the distal rigid straight portion 12 to provide a straight portion of the elongated shaft assembly with a sufficient length accommodate a fastener and to permit the actuation force from the fastener deployment system to be applied to that fastener in the same direction as the fastener deployment direction. Without wishing the bound by theory, this may result in reduced actuation forces required to deploy a fastener from the surgical instrument. While a surgical instrument 2 including a distal rigid straight portion 12 has been described herein, and depicted in figures, it should also be understood that embodiments are envisioned in which the articulable portion 8 extends all the way to the distal end of the elongated shaft assembly 6 such that the surgical instrument does not include a distal rigid straight portion.

FIG. 2 depicts an enlarged view of the distal end of the elongated shaft assembly 6 of FIG. 1 including the articulable section 8. In the depicted embodiment, the elongated shaft assembly 6 includes coaxially aligned first, second, and third tubular members. The depicted tubular members include an inner tubular member 20a, an intermediate tubular member 20b, and a rotatable outer tubular member 20c. In the embodiment depicted in figures, the inner tubular member 20a and intermediate tubular member 20b are axially affixed to one another at a distal position 136 distally located from the articulable portion 8. However, the rotatable outer tubular member 20c may, or may not, be axially affixed to either of the other tubular members depending on the particular embodiment. In the depicted embodiment, the inner tubular member 20a may be biased relative to the intermediate tubular member 20b to articulate the articulable portion 8 of the surgical instrument. Additionally, as described in more detail below, the outer tubular member 20c may be rotated relative to the other tubular members to prevent articulation of the articulable portion 8.

FIGS. 3A-5A present side views of the various tubular members that are rotated 90° between the paired figures to better visualize the flexible portions of the tubular members.

Figure 3A:
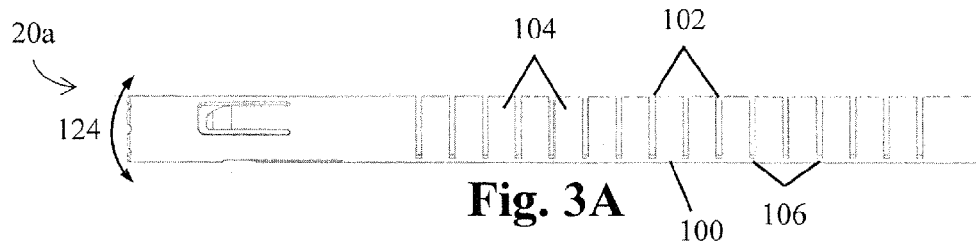
FIG. 3A is a schematic side view of the inner tubular member.
Figure 3B:
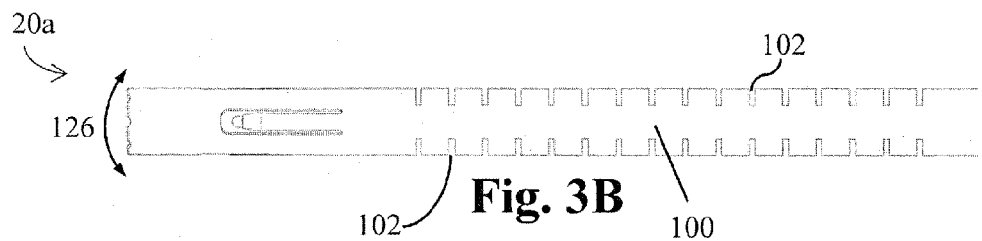
FIG. 3B is a schematic side view of the inner tubular member of FIG. 3A rotated 90°.

FIGS. 3A and 3B depict side and bottom views of the flexible portion of the inner tubular member 20a. The flexible portion of the inner tubular member 20a includes a single spine 100 extending along one side of the tubular member. The spine 100 corresponds to a continuous portion of the tubular member capable of transmitting axial forces along the length of the tubular member. The spine 100 may be defined by a series of slots 102 formed in the inner tubular member 20a. The spine 100 and the slots 102 may interact to form a plurality of flexible segments 104 joined together by a plurality of living hinges 106. The adjacent flexible segments 104 may be pivoted relative to one another about the intervening living hinges 106. It is this relative pivoting of the individual flexible segments 104 that imparts flexibility to the inner tubular member 20a. In addition, it is the orientation of the spine 100 and the slots 102 that define the preferential bending direction 124 about an axis of rotation of the living hinges 106. Without wishing to be bound by theory, the living hinges 106 exhibit increased bending resistance in directions other than those corresponding to pivoting of the living hinges 106 about the axes of rotation of the living hinges 106. Thus, directions in which the living hinges 106 exhibit increased stiffness may be viewed as corresponding to directions of bending resistance. In the depicted embodiment, a direction of bending resistance 126 may correspond to a direction that is perpendicular to the preferential bending direction and parallel to the axes of rotation of the living hinges 106 of the inner tubular member 20a.

Figure 4A:
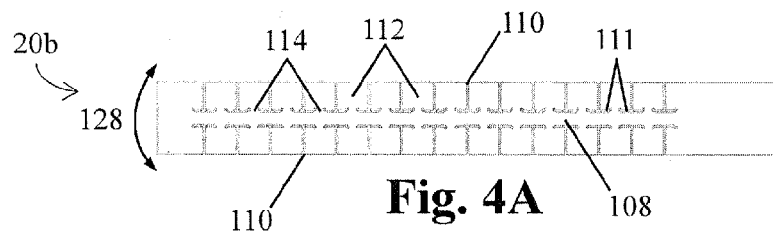
FIG. 4A is a schematic side view of the intermediate tubular member.
Figure 4B:
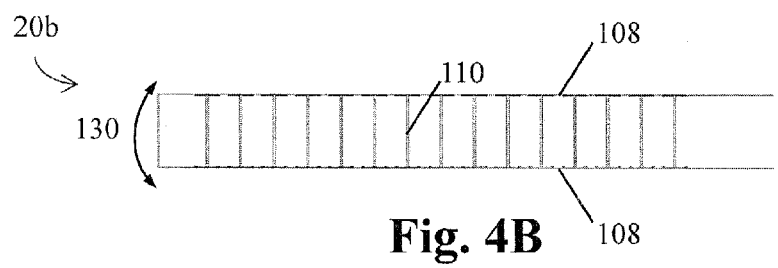
FIG. 4B is a schematic side view of the intermediate tubular member of FIG. 4A rotated 90°.

FIGS. 4A and 4B depict side and bottom views of the intermediate tubular member 20b. The intermediate tubular member 20b may be sized and shaped to accommodate the inner tubular member 20a when they are coaxially disposed in the assembled elongated shaft assembly. Similar to the above, the intermediate tubular member 20b may include a flexible portion defined by a plurality of slots 110 formed in the tubular member. However, in contrast to the inner tubular member, the depicted embodiment of the intermediate tubular member 20b includes two spines 108 that are defined by the slots 110 arranged on both sides of the two spines. In the depicted embodiment, the spines 108 extend distally along the flexible portion of the tubular member and are arranged on opposite sides of the tubular member, though other arrangements of the spines relative to one another are also possible. The depicted arrangement of the spines 108 and the slots 110 results in two separate sets of adjacent flexible segments 112 located above and below the spines 108. Each of the flexible segments 112 are pivotable about living hinges 114 formed between the junctions of the spines 108 and the slots 110. In some embodiments, and as depicted in the figures, each slot 110 may be associated with one or more secondary slots 111. The depicted secondary slots 111 are horizontally arranged slots located at the ends of the slots 110. Without wishing to be bound by theory, the secondary slots 111 may reduce the amount of material corresponding to the living hinges 114 which may impart greater flexibility to the flexible segments 112 for a given articulation force. While the secondary slots have been depicted as being horizontal slots located at the junction between the spines and flexible segments, other arrangements are also possible.

Without wishing to be bound by theory, due to the inclusion of two spines 108 located on opposite sides of the intermediate tubular member, the preferential bending direction and direction of bending resistance are different than that described above with regards to inner tubular member 20a. More specifically, the inclusion of the two spines 108 results in the living hinges 114 having axes of rotation that are oriented perpendicular to the spines in a direction that is parallel to a plane extending between the spines 108 (i.e. the axes of rotation extend between the two opposing spines). In addition, due to the symmetry of the slot patterns on either side of the spines, the living hinges 114 located above and below the spines 108 have axes of rotation that are aligned with one another. Consequently, the individual flexible segments 112, and the overall flexible portion of the intermediate tubular member 20b, exhibit a preferential bending direction 128 that corresponds to a direction of rotation around the living hinges 114 which is perpendicular to the plane extending between the spines 108.

Due to the individual flexible segments 112 of the intermediate tubular member 20b being associated with two spines 108 on either side of the tubular member, the intermediate tubular member 20b also exhibits directions of increased bending resistance that are different than described above with regards to the inner tubular member 20a. Without wishing to be bound by theory, the intermediate tubular member 20b exhibits an increased bending resistance in a direction that is parallel to the plane extending between the two spines. The observed increase in bending resistance may be due to the spines on either side of the tubular member resisting extension and contraction of the tubular member as might occur during bending of the tubular member in a direction that is parallel to the plane extending between the two spines. Further, each of the flexible segments 112 are connected to both of the spines 108 on either side of the tubular member. Thus the movement of the two spines 108 relative to one another may be further limited since the spines are in effect fixed to one another at points extending along their lengths which may lead to an additional increase in the resistance to bending of the tubular member. This behavior may be contrasted with the flexible segments 112 and slots 110 which are specifically configured to accommodate both extension and contraction of the tubular member to facilitate bending of the elongated shaft assembly. In view of the above, the inclusion of the two spines 108 in the intermediate tubular member 20b results in a direction of increased bending resistance 130 that is perpendicular to the preferential bending direction 128 and the direction of rotation of the living hinges 114. Additionally the direction of increased bending resistance 130 may also be parallel to the plane extending between the two spines 108 as well as axes of rotation for the living hinges 114.

Figure 5A:
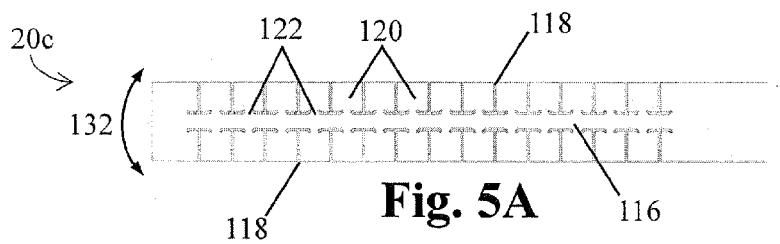
FIG. 5A is a schematic side view of the outer tubular member.
Figure 5B:
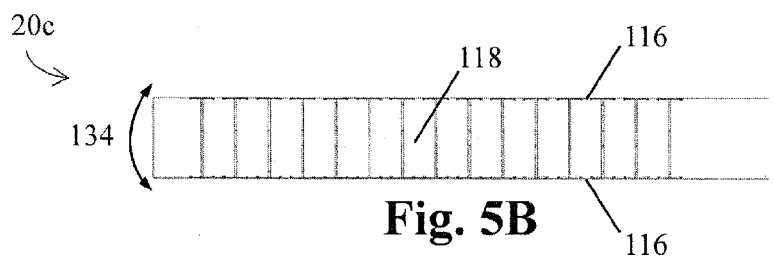
FIG. 5B is a schematic side view of the outer tubular member of FIG. 5A rotated 90°.

FIGS. 5A and 5B depict the outer tubular member 20c which may be sized and shaped to accommodate the inner tubular member 20a and the intermediate tubular member 20b when they are coaxially disposed within the elongated shaft assembly 6. In addition, the depicted embodiment of the outer tubular member 20c may exhibit a similar arrangement of spines 116, slots 118, flexible segments 120, and living hinges 122 as described above with regards to the intermediate tubular member 20b. Consequently, similar to the intermediate tubular member 20b, the outer tubular member 20c may exhibit a preferential bending direction 132 that corresponds to a direction of rotation around the living hinges 122 and is perpendicular to a plane extending between the spines 116. Additionally, the outer tubular member 20c may exhibit a direction of increased bending resistance 134 which is perpendicular to the preferential bending direction 132. The direction of increased bending resistance 134 may also be parallel to the plane extending between the two spines 116 and the axes of rotation of the living hinges 122.

FIGS. 6A-7B depict one embodiment of how the elongated shaft assembly 6 may be articulated. For the sake of clarity in illustrating how the elongated shaft assembly is articulated, only the inner tubular member 20a and the intermediate tubular 20b are depicted in the figures.

In the depicted embodiment, the inner tubular member 20a may be coaxially disposed within the intermediate tubular member 20b. The flexible portions of the tubular members 20a and 20b may be aligned to form articulable portion 8. Further, the tubular members 20a and 20b may be axially affixed to one another at the distal position 136 which is distally located relative to the articulable portion 8. The tubular members may be affixed to one another using welding, brazing, soldering, adhesives, mechanical interlocking features, or any other appropriate method capable of affixing the tubular members to one another. It should be noted, that while the tubular members 20a and 20b may be axially affixed to one another at a distal position 136, the tubular members 20a and 20b may be free to move relative to one another at their proximal ends. As depicted in figures, the tubular members 20a and 20b may also include retaining elements 126 and 128 to interact with components within the handle to bias the inner tubular member 20a relative to the intermediate tubular member 20b.

Figure 6A:
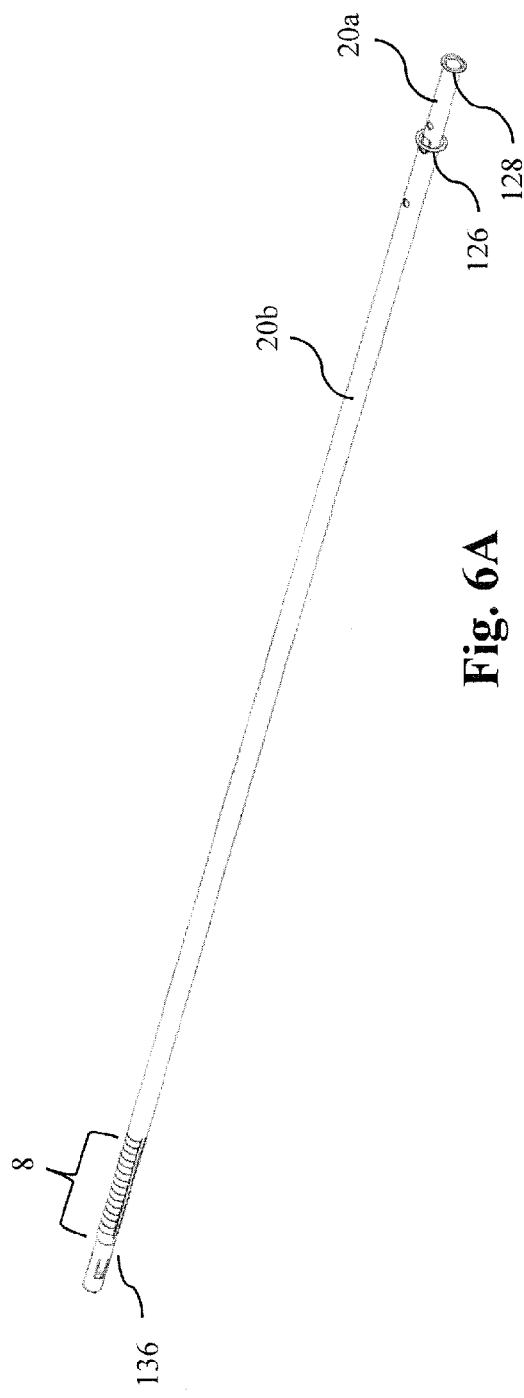
FIG. 6A is a schematic perspective view of the inner and intermediate tubular members in an unarticulated position.
Figure 6B:
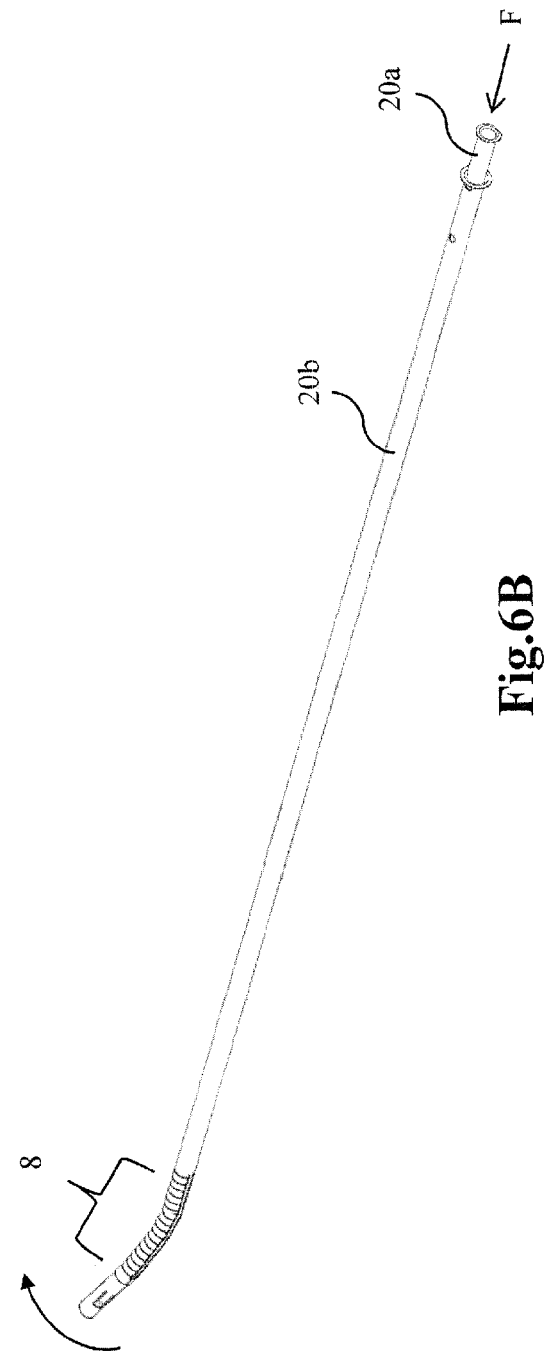
FIG. 6B is a schematic perspective view of the inner and intermediate tubular members in an articulated position.

FIG. 6A depicts the tubular members 20a and 20b in the unbiased position in which neither tubular member is under compression or tension. When a user wishes to articulate articulable portion 8, inner tubular member 20a may be distally displaced relative to the intermediate tubular member 20b by a force F, see FIG. 6B. Depending upon the particular embodiment, a force directed in the distal direction may result in articulation in a first direction and a force directed in the proximal direction may result in articulation in a second direction opposite from the first. Without wishing to be bound by theory, as the inner tubular member 20a is displaced relative to the intermediate tubular member 20b, a compressive or tensile force is created in the inner tubular member 20a and a corresponding tensile or compressive force is created in the intermediate tubular member 20b depending on the direction of the relative displacement. It is the interaction of the compressive and tensile forces with the flexible portions of the tubular members that results in the articulation depicted in FIG. 6B.

FIGS. 7A-7B present an external perspective view, as well as a cross-sectional view, of the articulable portion 8 formed by the inner tubular member 20a and the intermediate tubular member 20b to better illustrate how the articulation motion is created by biasing the inner tubular member 20a relative to the intermediate tubular member 20b. As noted previously, the inner tubular member 20a and the intermediate tubular member 20b are axially affixed to one another at a distal position 136, but are free to move relative to one another at positions proximal to the distal position 136. Without wishing to be bound by theory, when a force is applied to one of the tubular members a compressive force is applied to one tubular member and a tensile force is applied to the other tubular member. It should be noted that the flexible segments 104 and 112 of the tubular members of the depicted embodiment do not carry the compressive and tensile loads applied to the tubular members since each flexible segment 104 and 112 is free to move relative to the other adjacent flexible segments. Instead, the spines 100 and 108 carry the compressive and tensile loads applied to the tubular members 20a and 20b. In addition to carrying the compressive and tensile loads, the spines 100 and 108 tubular members remain the same length when a biasing force is applied for the reasons noted previously. In contrast, the flexible segments 104 and 112 of the tubular members may expand and contract relative to one another when a biasing force is applied.

As best illustrated by FIG. 7B, and without wishing to be bound by theory, when a force is applied to the inner tubular member 20a, the spine 100 applies the force to one side of the elongated shaft assembly at the distal position 136 where the tubular members 20a and 20b are axially affixed to one another. A corresponding force is applied to the elongated shaft assembly by the spines 108 of the intermediate tubular member 20b which are spaced from the spine 100 of the inner tubular member 20a. This application of spaced apart forces from the spine 100 and the spines 108 creates a bending moment in the elongated shaft assembly 6 resulting in compression of the flexible segments 104 and 112 of the tubular members on one side of the articulable portion 8. Since the spines 100 and 108 stay the same size while the flexible segments 104 and 112 pivot to accommodate the applied bending moment, articulable portion 8 articulates. It should be noted, that if a force is applied to the inner tubular member in the opposite direction, the flexible segments 104 and 112 would expand on one side of the articulable portion 8 to articulate the elongated shaft assembly 6 in the opposite direction.

In addition to looking at how the spines of the tubular members carry the applied forces to articulate the articulable portion 8, the articulation of articulable portion 8 may also be described using the neutral bending axes of the tubular members relative to one another. Without wishing to be bound by theory, when an axially oriented force is applied to an object, the force may be approximated as a force applied along the neutral bending axis. Within the articulable portion 8, the neutral bending axis 138 of the inner tubular member 20a corresponds to the spine 100. In contrast, due to the inclusion of the two distally extending spines 108 located on opposite sides of the intermediate tubular member 20b, intermediate tubular member 20b has a neutral bending axis 140 that corresponds to the central axis of the intermediate tubular member 20b. Thus, a biasing force applied to one of the tubular members may result in equal and opposite forces being applied along the two offset neutral bending axes. The forces applied to the tubular members along the offset neutral bending axes may again create a bending moment within the elongated shaft assembly 6 to articulate the articulable portion 8 as described above.

It should be understood that while tubular members with particular patterns of slots and spines have been depicted in the figures and described herein, other arrangements of tubular members with different patterns of slots and spines as well as different numbers of spines are also possible to provide the desired articulation of the surgical instrument. Further, other types of articulation may be incorporated into the surgical instrument as the current disclosure is not limited to any particular form of articulation control or any particular form of articulation.

Turning now to how an articulation locking mechanism might operate, FIGS. 8-11 depict the elongated shaft assembly 6 with the rotatable outer tubular member 20c which may be rotated between an articulable configuration and a non-articulable configuration.

Figure 8:
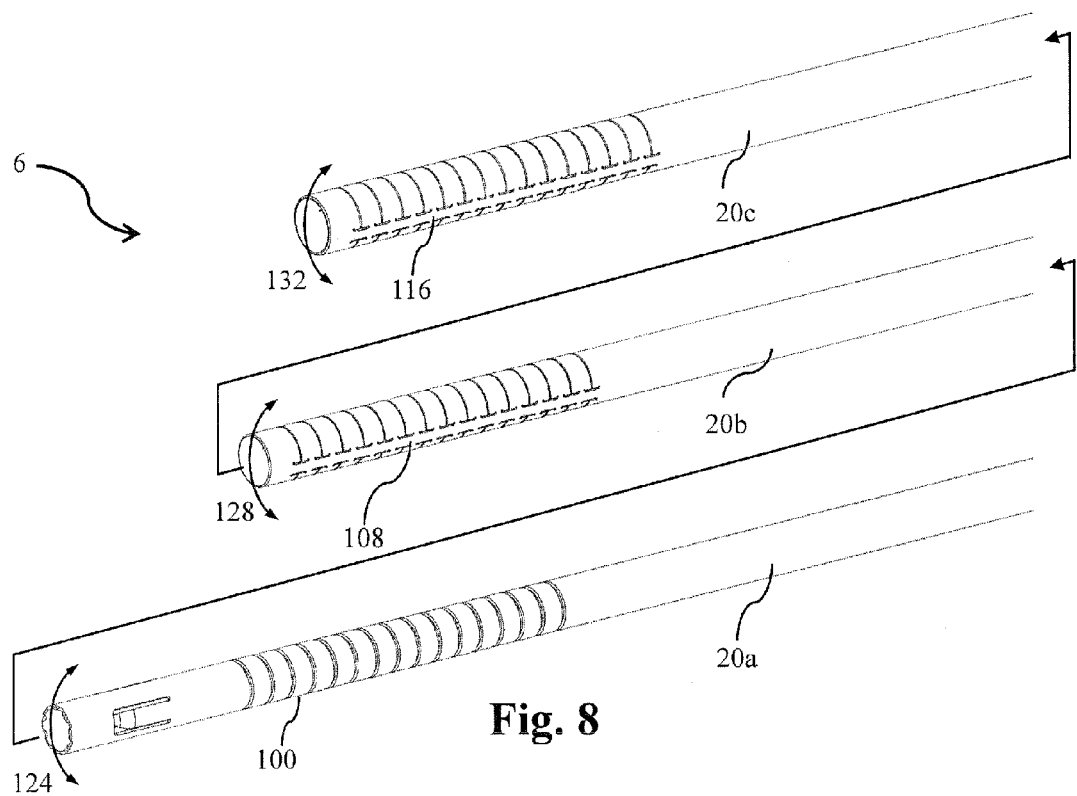
FIG. 8 is an exploded schematic representation of the tubular members in the articulable configuration.
Figure 9:
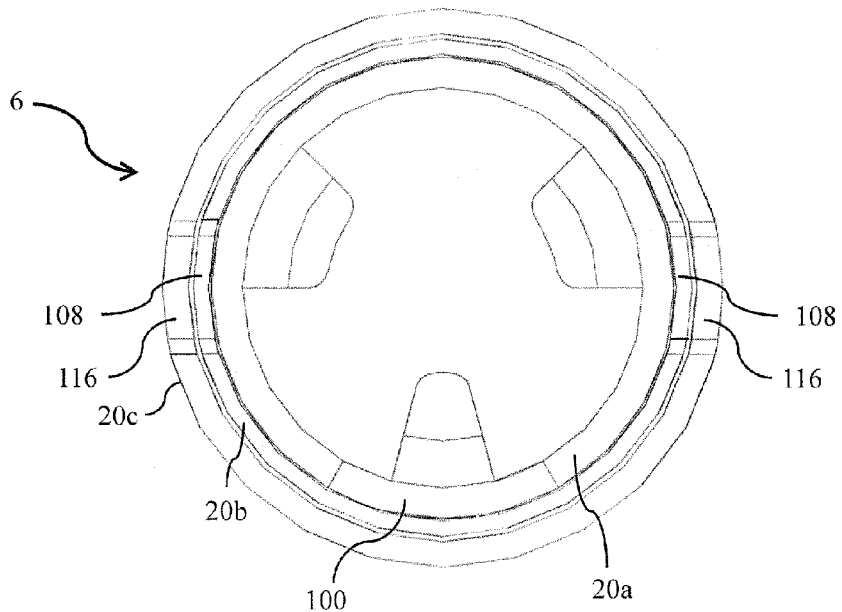
FIG. 9 is a schematic cross-sectional view of the tubular members in the articulable configuration.

FIGS. 8-9 depict an exploded schematic view, as well as a cross-sectional view, of the elongated shaft assembly 6 in the articulable configuration. In the depicted embodiment, the inner tubular member 20a is disposed within the intermediate tubular member 20b which is disposed within the outer tubular member 20c. In the depicted configuration, the preferential bending directions 124, 128, and 132 of each of the tubular members 20a-20c are aligned with one another. Correspondingly, the spine 100 of inner tubular member 20a is perpendicular to the spines 108 of the intermediate tubular member 20b and the spines 116 of the outer tubular member 20c. In the depicted embodiment, the articulation direction of the elongated shaft assembly 6 may correspond to the preferential bending direction 124 of the inner tubular member 20a. Consequently, the preferential bending direction 132 of the outer tubular member 20c is aligned with the articulation direction of the elongated shaft assembly 6. Since the preferential bending directions of each of the tubular members are aligned with one another as well as being aligned with the articulation direction of the elongated shaft assembly 6, the elongated shaft assembly 6 may be articulated when it is biased by the associated articulation control.

Figure 10:
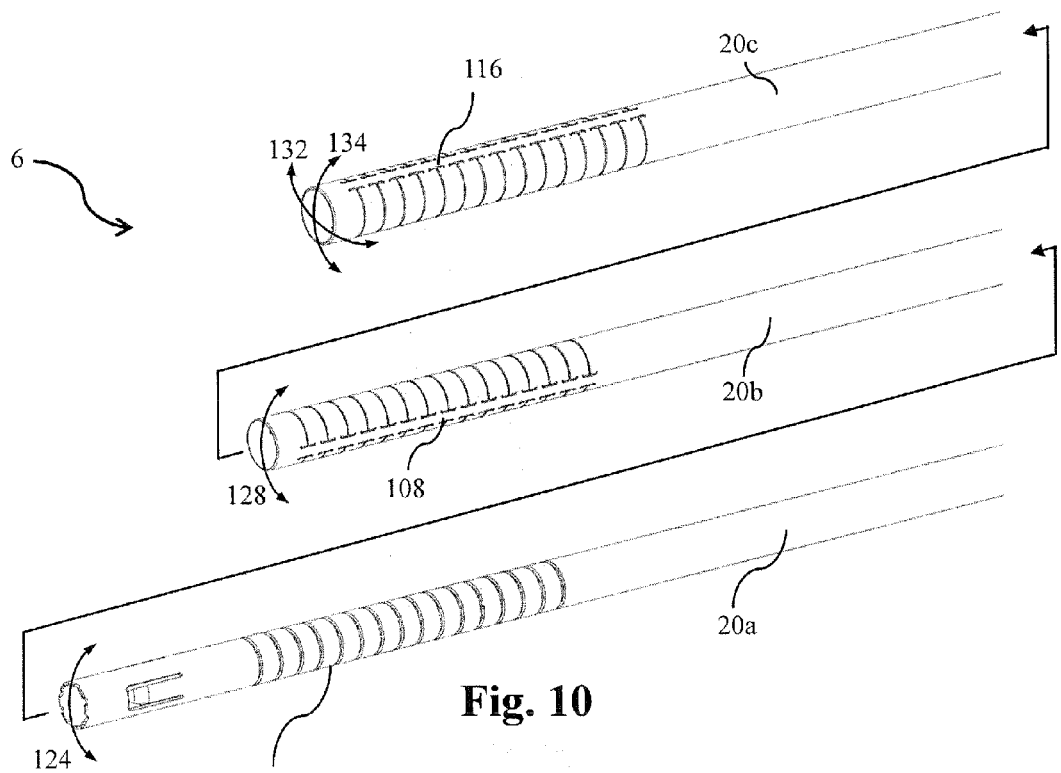
FIG. 10 is an exploded schematic representation of the tubular members in the locked configuration.
Figure 11:
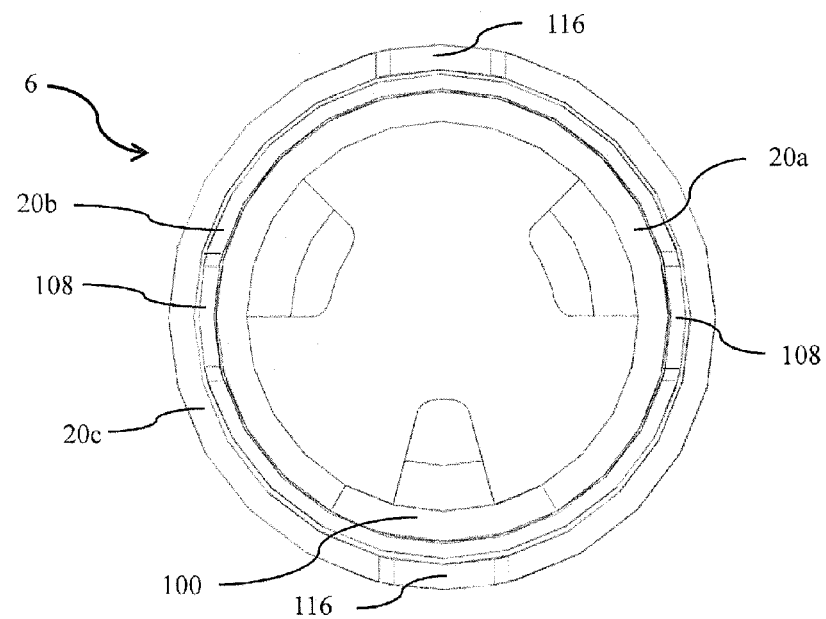
FIG. 11 is a schematic cross-sectional view of the tubular members in the locked configuration.

When it is desired to prevent articulation of the elongated shaft assembly 6, outer tubular member 20c may be rotated relative to the inner tubular member 20a and intermediate tubular member 20b to the non-articulable configuration as depicted in FIGS. 10-11. While this rotation may be of any appropriate angle, in the depicted embodiment the outer tubular member 20c is rotated approximately 90° between the articulable configuration and the non-articulable configuration. As illustrated in the figures, the preferential bending directions 124 and 128 of the inner tubular member 20a and the intermediate tubular member 20b remain aligned for the purposes of articulation. However, the preferential bending direction 132 of the outer tubular member 20c is no longer aligned with the preferential bending directions 124 and 128. Instead, the direction of bending resistance 134 of the outer tubular member 20c is aligned with the preferential pending directions 124 and 128. Further, the spine 100 of the inner tubular member 20a is perpendicular to the spines 108 of the intermediate tubular member 20b and aligned with the spines 116 of the outer tubular member 20c. As noted above, the articulation direction of the elongated shaft assembly 6 may correspond to the preferential bending direction 124 the inner tubular member 20a. Consequently, the direction of bending resistance 134 is aligned with the articulation direction of the elongated shaft assembly 6 in the depicted embodiment. Due to the direction of bending resistance 134 of the outer tubular member 20c being aligned with the articulation direction, as well as the preferential bending directions of the other tubular members 20a and 20b, the outer tubular member 20c may prevent articulation of the elongated shaft assembly in the depicted configuration.

It should be understood that while a particular arrangement of spines and slots have been described above with regards to the tubular members to provide the desired preferential bending directions and directions of bending resistance, the current disclosure is not limited to only the depicted tubular members. For example, in addition to use with tubular members including a pattern of slots and spines, the current disclosure may be used with tubular members including flexible sections comprised of individual articulating links that are constructed and arranged to be displaceable in one or more preselected directions. Consequently, the current disclosure should be viewed generally as applying to the articulation of any device including any appropriately adapted component that is capable of being moved to selectively align a preferential bending direction and a direction of bending resistance with an articulable portion of the device to selectively permit or prevent articulation of the device.

The above embodiments have depicted the tubular member used to selectively prevent articulation of the surgical instrument as being located at the exterior of the elongated shaft assembly. However, the current disclosure is not limited as to the particular position of the tubular member. For example, the elongated shaft assembly may include a tubular member to selectively prevent articulation that is arranged as an interior tubular member, an intermediate tubular member, or an exterior tubular member.

In some embodiments, it may be advantageous to provide an elongated shaft assembly that may be articulated and selectively prevented from articulating using two tubular members instead of the three tubular members as disclosed above. In such an embodiment, the tubular members may be constructed and arranged to provide a similar functionality as described above with regards to the inner tubular member and the intermediate tubular member to articulate the elongated shaft assembly. In addition, similar to the embodiment described above, the tubular members may be axially affixed to one another at a distal position to facilitate articulation of the elongated shaft assembly. However, in addition to being axially affixed to one another to facilitate articulation of the elongated shaft assembly, the tubular members may also be rotatable relative to one another to selectively permit or prevent articulation of the elongated shaft assembly. Similar to the above described embodiments, the elongated shaft assembly might be articulable when the preferential bending directions of the tubular members are aligned with one another. Further, the elongated shaft assembly may be prevented from articulating when a direction of bending resistance of one tubular member is aligned with the preferential bending direction of the other tubular member and/or the articulation direction of the elongated shaft assembly 6.

The two tubular members of the above embodiment may be rotatably coupled while being axially affixed to one another at a distal position using any appropriate connection. For example, in one embodiment, the tubular members may include a boss and a corresponding shelf that would axially constrain the tubular members relative to one another while permitting rotation. In another embodiment, the tubular members may include interlocking mechanical elements that axially constrain the tubular members while permitting rotation of the tubular members relative to one another. One example of such an embodiment may include a tubular member with a lip at a distal end that is captured by a corresponding feature on the other tubular member. It should be understood that other configurations are possible and that the current disclosure is not limited to only the rotatable couplings noted above. In addition, in some embodiments, it may be desirable to decrease the friction present within the rotatable coupling to aid in the rotation of the tubular members relative to one another. Consequently, it may be advantageous to include features to facilitate the rotation of the tubular members relative to another such as lubrication, bearings, low friction materials, and other appropriate features.

In some embodiments, it may be desirable to provide a different configuration or pattern of slots and spines on one or more of the tubular members. Different arrangements of slots and spines on the tubular members may provide benefits including different articulation characteristics, reduced interference between moving components, increased bending resistance in selected directions, decreased bending resistance in selected directions, increased articulation ranges, complex articulation directions and other benefits as would be obvious to one of ordinary skill in the art. The different configurations and patterns of the slots and spines may include helically arranged slots, slanted slots, a plurality of distally extending spines circumferentially arranged around the tubular members, spines oriented at an angle relative to the tubular member axis, and any other appropriate pattern or arrangement as the current disclosure is not limited to any particular construction. In addition, the tubular members may be formed using laser cutting, grinding, water cutting, milling, or any other appropriate method.

Without wishing to be bound by theory, large articulation angles of the tubular members may result in contact between adjacent flexible segments which may prevent additional articulation of the elongated shaft assembly. However in some embodiments, large articulation angles may be desirable for a particular use. Consequently, in some embodiments, large articulation angles may be accommodated by providing longer articulable portions capable of articulating to larger angles while maintaining the same angular displacement per flexible segment. Alternatively, in some embodiments, the maximum angular displacement per flexible segment may be increased to accommodate the large articulation angle. The maximum angular displacement per flexible segment may be increased by increasing a width of the slots, or by including reliefs or cutouts on the flexible segments to increase the angle at which contact occurs between adjacent flexible segments. Combinations of the above embodiments may also be used (e.g., a longer articulable portion and reliefs formed on the flexible segments). While the above embodiments are directed to increasing the permissible articulation angle, in some embodiments, it may be desirable to limit the articulation angle of the elongated shaft assembly. In such an embodiment, the length of the articulable portion and/or the maximum angular displacement per flexible segment may be selected to provide a desired maximum articulation angle.

In some embodiments, and as noted above, it may be desirable to articulate the surgical instrument in more than one direction. For example, it may be desirable to articulate the surgical instrument in a vertical direction, a horizontal direction, or a direction between the vertical and horizontal directions. These complex articulations may be provided in any number of ways. For example, in one embodiment, three or more tubular members including appropriately oriented spines and slots might be used to provide articulation in multiple directions. Alternatively, a flexible tubular member may include appropriate articulation mechanisms such as wires or slats capable of articulating the tubular member in multiple directions. In addition to articulating the surgical instrument in multiple directions, it may also be desirable to selectively permit or prevent the articulation of the surgical instrument in one, or all, of the articulable directions. In such an embodiment, one or more tubular members may be used to permit or prevent the articulation of the surgical instrument in any one, or all, of the articulation directions. For example, a single tubular member may include a plurality of preferential bending directions as well as a plurality of directions of bending resistance which may be selectively aligned with the plurality of articulation directions to selectively permit or prevent articulation of the surgical instrument in one, or all of the articulable directions. Alternatively, a plurality of tubular members each including a preferential bending direction and a direction of bending resistance might be used. In such an embodiment, each of the plurality of tubular members may be oriented to selectively permit or prevent articulation of the surgical instrument in a particular direction. Other configurations using a plurality of tubular members are also possible.

FIG. 12 depicts the elongated shaft assembly 6 including the inner tubular member, the intermediate tubular member, and the outer tubular member, as described above, incorporated in a surgical instrument 2. In the depicted embodiment, the elongated shaft assembly 6 extends distally from the handle 4 and is associated with an articulation control 10. More specifically, articulation control 10 is a rotatable component that includes a slot 202. The slot 202 is sized and shaped to interact with a corresponding pin 204 associated with an articulation coupling 200. The articulation coupling 200 is coupled to the elongated shaft assembly 6 to control the articulation of the articulable portion 8 depicted in FIG. 1 by selectively displacing one of the inner tubular member and the intermediate tubular member as noted above. More specifically, as the articulation control 10 is rotated, the pin 204, the articulation coupling 200, and the associated tubular member are selectively moved in either a proximal or distal direction to articulate, or straighten, the articulable portion 8.

In some instances, and as depicted in the figure, the slot 202 may be shaped to provide two resting positions for pin 204. These positions may correspond to the unarticulated position and the fully articulated position of articulable portion 8. In other embodiments, the slot 202 may be shaped and arranged to include more than two resting positions to provide multiple articulated positions of articulable portion 8. Alternatively, the slot 202 may provide a gradual transition between the unarticulated and fully articulated position. In such an embodiment, the articulation control 10 may include a locking mechanism or have sufficient friction to maintain the pin 204, and correspondingly the articulable portion 8, at any desired articulation angle between the unarticulated and fully articulated position. Additionally, as noted above, in some instances it may be desirable to provide articulation in two directions (i.e. up and down). In such an embodiment, the slot 202 may be shaped and arranged to include a first resting position corresponding to the unarticulated position as well as one or more resting positions on either side of that first resting position to enable articulation of the articulable portion 8 in both directions.

While a specific articulation control and articulation coupling have been depicted in the figures and described herein, the current disclosure is not limited to only the depicted embodiments. Therefore, it should be understood that any appropriate articulation coupling and articulation control could be used. Further, any appropriate method for transferring movement of the articulation control to the articulation coupling and/or articulable portion 8 could also be used. The articulation control may also be moved between the various articulation positions using any appropriate motion including linear movement in a proximal and distal direction, linear movement in the vertical direction, linear movement in the horizontal direction, rotation in a proximal or distal direction, rotation in the vertical direction, and/or rotation in the horizontal direction. Combinations of the above movements, as well as other types of movements, to move the articulation control between two or more positions are also possible.

In order to control the rotation of the outer tubular member 20c to selectively permit or prevent articulation of the surgical instrument, the handle 4 may include a rotatable collar 205 associated with the outer tubular member 20c. In the depicted embodiment, rotation of the rotatable collar 205 directly rotates the outer tubular member 20c relative to the articulable portion 8 of the elongated shaft assembly to selectively move the preferential bending direction of the outer tubular member 20c into and out of alignment with the articulation direction of the elongated shaft assembly 6. Consequently, rotation of the rotatable collar 205, and the associated outer tubular member 20c, may selectively permit, or prevent, articulation of the elongated shaft assembly 6. In some embodiments, the rotatable collar 205 may only be rotatable between an articulable position and a non-articulable position. Alternatively, the rotatable collar 205 may be positioned at any number of distinct positions between the articulable position and the non-articulable position to provide partial locking of the articulable portion of the elongated shaft assembly. To facilitate positioning of the rotatable collar 205, the rotatable collar 205 may include detent mechanisms, or any other appropriate feature, to facilitate the positioning and retention of the outer tubular member 20c in any number of preselected positions. However, embodiments not including a detent mechanism, or other appropriate feature to control the position of the outer tubular member 20c, are also envisioned. Further, while a particular rotatable collar has been depicted for controlling the positioning of the outer tubular member 20c, any appropriate construction capable of positioning the outer tubular member 20c in the desired orientation might be used. For example, both direct couplings such as the depicted rotatable collar as well as indirect couplings including transmissions might be used to move the outer tubular member 20c between the articulable position and the non-articulable position.

As noted previously, the surgical instrument 2 may also include a fastener deployment system as depicted in FIG. 12. The fastener deployment system 102 may be embodied in a number of different ways. However, in the particular embodiment depicted in FIG. 12 the fastener deployment system may include a trigger 14, a rigid linkage 206, a shuttle 208, a power assist device 210, and a driveshaft 212 as well as other components that are not depicted. When the surgical instrument 2 is actuated, actuation of the trigger 14 may distally displace the rigid linkage 206 to distally displace the shuttle 208 and store energy in the power assist device 210. After a preselected amount of actuation, the power assist device 210 may release the stored energy to distally accelerate driveshaft 212 and deploy a fastener from the distal end of the elongated shaft assembly 6.

The power assist device 210 may correspond to any appropriate construction capable of aiding in deploying a fastener from the elongated shaft assembly of the surgical instrument. Further, depending on the particular embodiment, the power assist device 210 may supply all of the power necessary to deploy a fastener, or it may only supply a portion of the power necessary to deploy a fastener. In one specific embodiment, the power assist device 106 corresponds to the power assist device disclosed in application Ser. No. 13/804,043 entitled POWER ASSIST DEVICE FOR A SURGICAL INSTRUMENT filed on the same day as the current application. While a surgical instrument including a power assist device has been depicted, in some embodiments, the surgical instrument 2 may not include a power assist device, in which case actuation of the trigger 14 may directly, or indirectly, displace driveshaft 212 to deploy a fastener from a distal end of the elongated shaft assembly 6.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A surgical instrument comprising:
    a handle; and
    an elongated shaft assembly extending distally from the handle, wherein the elongated shaft assembly includes an articulable portion with an articulation direction, and wherein the elongated shaft assembly includes a tubular member with a flexible portion with a preferential bending direction and a direction of bending resistance, wherein the tubular member permits articulation of the elongated shaft assembly when the preferential bending direction is aligned with the articulation direction.

2. The surgical instrument of claim 1, wherein the tubular member prevents articulation of the elongated shaft assembly when the direction of bending resistance is aligned with the articulation direction.

3. The surgical instrument of claim 1, wherein the tubular member is rotatable.

4. The surgical instrument of claim 1, wherein the direction of bending resistance is parallel to a plane extending between a first spine and a second spine located on opposite sides of the tubular member.

5. The surgical instrument of claim 1, wherein the preferential bending direction is provided by slots cut on one or more sides of the tubular member.

6. The surgical instrument of claim 1, wherein a distal end of the tubular member is free to move axially relative to the elongated shaft assembly.

7. The surgical instrument of claim 1, wherein the elongated shaft assembly comprises an inner tubular member and an outer tubular member disposed within the outer tubular member, wherein the inner and outer tubular members have offset neutral bending axes.

8. A surgical instrument comprising:
    a handle; and
    an elongated shaft assembly extending distally from the handle, the elongated shaft assembly comprising:
        a first tubular member including a first flexible portion with a first preferential bending direction;
        a second tubular member including a second flexible portion with a second preferential bending direction; and
        a third tubular member including a third flexible portion with a third preferential bending direction and a direction of bending resistance, wherein the first tubular member, the second tubular member, and the third tubular member are coaxially located, wherein the first tubular member and the second tubular member are axially fixed relative to one another at a position distal from the first flexible portion and the second flexible portion; and wherein the third tubular member is displaceable relative to the first tubular member and the second tubular member.

9. The surgical instrument of claim 8, wherein the third tubular member is rotatable relative to the first tubular member and the second tubular member.

10. The surgical instrument of claim 8, wherein a distal end of the third tubular member is free to move axially relative to the first tubular member and the second tubular member.

11. The surgical instrument of claim 8, wherein the first tubular member and the second tubular member are disposed within the third tubular member.

12. The surgical instrument of claim 8, wherein the first preferential bending direction and the second preferential bending direction are aligned.

13. The surgical instrument of claim 8, wherein the third tubular member prevents articulation of the first tubular member and the second tubular member when the direction of bending resistance is aligned with at least one of the first preferential bending direction and the second preferential bending direction.

14. The surgical instrument of claim 8, wherein the third tubular member permits articulation of the first tubular member and second tubular member when the third preferential bending direction is aligned with the first preferential bending direction and the second preferential bending direction.

15. The surgical instrument of claim 8, wherein a proximal end of the first tubular member is axially displaceable relative to a proximal end of the second tubular member to articulate the first flexible portion and the second flexible portion.

16. A surgical instrument comprising:
    a handle; and
    an elongated shaft assembly extending distally from the handle, the elongated shaft assembly comprising:
        a first tubular member including a first flexible portion with a first spine;
        a second tubular member including a second flexible portion with a second spine, wherein the first tubular member and the second tubular member are axially fixed relative to one another at a position distal from the first flexible portion and the second flexible portion; and
        a third tubular member including a third flexible portion with a third spine and a fourth spine, wherein the first tubular member, the second tubular member, and the third tubular member are coaxially located, and wherein the third tubular member is displaceable relative to the first tubular member and the second tubular member.

17. The surgical instrument of claim 16, wherein the third tubular member is rotatable relative to the first tubular member and the second tubular member.

18. The surgical instrument of claim 16, wherein a distal end of the third tubular member is free to move axially relative to the first tubular member and the second tubular member.

19. The surgical instrument of claim 16, wherein the first tubular member and the second tubular member are disposed within the third tubular member.

20. The surgical instrument of claim 16 wherein the second tubular member includes a fifth spine, and wherein the second spine and the fifth spine are perpendicular to the first spine to permit articulation of the first flexible portion and the second flexible portion.

21. The surgical instrument of claim 16, wherein the third tubular member prevents articulation of the first tubular member and second tubular member when the third spine and the fourth spine are aligned with the first spine.

22. The surgical instrument of claim 16, wherein the third tubular member permits articulation of the first tubular member and second tubular member when the third spine and the fourth spine are perpendicular to the first spine.

23. The surgical instrument of claim 16, wherein a proximal end of the first tubular member is axially displaceable relative to a proximal end of the second tubular member to articulate the first flexible portion and the second flexible portion.

24. A surgical instrument comprising:
a handle;
an elongated shaft assembly extending distally from the handle, the elongated shaft assembly including:
a first tubular member including a first flexible portion with a first spine;
a second tubular member including a second flexible portion with a second spine and a third spine, wherein the first tubular member and the second tubular member are coaxially located, wherein the first tubular member and the second tubular member are axially fixed relative to one another at a position distal from the first flexible portion and the second flexible portion, and wherein the second tubular member is rotatable relative to the first tubular member.

25. The surgical instrument of claim 24, wherein the first tubular member is disposed within the second tubular member.

26. The surgical instrument of claim 24, wherein the second tubular member prevents articulation of the elongated shaft assembly when the second spine and third spine are aligned with the first spine.

27. The surgical instrument of claim 24, wherein the second tubular member permits articulation of the elongated shaft assembly when the second spine and third spine are perpendicular to the first spine.

28. The surgical instrument of claim 24, wherein a proximal end of the first tubular member is axially displaceable relative to a proximal end of the second tubular member to articulate the elongated shaft assembly.

* * * * *